United States Patent [19]

Doll

[11] Patent Number: 5,078,716

[45] Date of Patent: Jan. 7, 1992

[54] ELECTROSURGICAL APPARATUS FOR RESECTING ABNORMAL PROTRUDING GROWTH

[76] Inventor: Larry F. Doll, 313 Woodland Ave., Haddonfield, N.J. 08033

[21] Appl. No.: 522,264

[22] Filed: May 11, 1990

[51] Int. Cl.$^5$ .............................................. A61B 17/39
[52] U.S. Cl. ........................................ 606/47; 606/48
[58] Field of Search ............................. 606/47, 48, 50

[56] References Cited

U.S. PATENT DOCUMENTS

| 4,202,338 | 5/1980 | Bitrolf | 606/47 |
| 4,493,320 | 1/1985 | Treat | 606/47 |
| 4,905,691 | 3/1990 | Rydell | 606/47 |

FOREIGN PATENT DOCUMENTS

| 2514501 | 10/1976 | Fed. Rep. of Germany | 606/50 |
| 3220940 | 12/1983 | Fed. Rep. of Germany | 606/47 |

*Primary Examiner*—Lee S. Cohen
*Attorney, Agent, or Firm*—Bernard Malina

[57] ABSTRACT

The present invention relates to surgical instruments for removing protruding tissue such as tonsils, warts, polyps and like, from the body, more specifically, it relates to loop type snare instruments supplying a high frequency electrical current for coagulation and cutting during the removal of these body growths.

In a primary embodiment of the invention, a loop is provided which is made of electrically conductive wire connected to a loop made of electrically conductive wire within a tubular insulated sheath. The wire is connected to a handle assembly that will allow the loop to be extended from or retracted into the distal end of the tubular insulated sheath. The loop is covered over a major portion of its circumference by an insulating material, leaving only a minor portion of its circumference uninsulated at the portion of the loop most distal from the tubular sheath, and electrically active. The handle mechanism includes an electrical connector for connection of the conductive wire to an electrosurgical generator.

21 Claims, 2 Drawing Sheets

ELECTROSURGICAL APPARATUS FOR RESECTING ABNORMAL PROTRUDING GROWTH

BACKGROUND OF THE INVENTION

There is a continuing need for a safe and effective surgical snare apparatus for the removal of protruding tissue such as tonsils, warts, polyps and the like from the body. Conventional surgical snares operate by pulling a conductive wire loop, surrounding a tissue protrusion, into a tubular sheath. These surgical snares are typically modified to allow connection of an electrical source to the conductive wire loop, and the tubular outer sheath is typically made of a non-conductive material. When the wire loop is snug around the tissue to be removed, high frequency electrical current is delivered to the tissue in contact with the conductive wire loop from an appropriate electrosurgical generator. The high frequency electrical current is concentrated on the tissue at the point of contact of the wire loop; it travels through the body at lower concentrations, to a large surface area dispersive electrode, and returns to the electrosurgical generator, thus completing the circuit.

For a conventional electrosurgical snare to function properly, the critical requirement is a proper current density at the interface between the wire loop and the body tissue. This current density must be sufficiently high to allow effective heating of the intra cellular fluid, drying the tissue to prevent hemorrhage. As a tissue in contact with the snare wire is coagulated, its electrical resistance increases. The conventional electrosurgery generator, to which the snare is attached, is capable of producing voltages as high as several thousand volts. This allows energy to arc across the high resistance tissue, resulting in electrosurgical cutting through the dry tissue. A user, skilled in the practice of this technique, tries to maintain the critical balance between the rate of tissue drying and the rate of high voltage arcing for electrosurgical cutting. The desired clinical result is the removal of the tissue without hemorrhages at the site of removal.

There are numerous disadvantages to the conventional electrosurgical snare. It is difficult for the user of a conventional snare to maintain the correct level of electrosurgical current density with varying size growths. For instance, if the snare loop is fully extended around a large piece of tissue, initial electrosurgical power levels considerably higher than typically used will be required to obtain the proper current density, along the interface betwen the wire loop and the tissue, to start the procedure. As this procedure proceeds, and the wire loop is pulled back into the tubular sheath, the diameter of the exposed wire loop decreases, resulting in a potentially dangerous increase in current density along the remaining exposed wire to tissue interface. This results in a rapid increase in the rate of electrosurgical cutting of the tissue; and also results in a corresponding decrease in the quality of coagulation along the resected surface. This can result in dangerous hemorrhage of the patient. Additionally, these higher initial power levels cause higher current densities at other points along the electrical pathway between the wire loop and the dispersive electrode in contact with the patient's body at another site. This can result in undesirable damage to other body organs and tissues.

Although this conventional type of electrosurgical snare is in wide use, it is impossible for the user to avoid the increase of the current density along the exposed wire loop as the loop is pulled into its sheath during the course of the removal of tissue. Because of the varying initial size of tissue growths to be removed, and the changing effective length of the electrically conductive wire during a procedure, it is very difficult to select an initial electrosurgical power level that will provide consistently predictable clinical results. Furthermore, since the electrical currents must travel from the contact point of the snare wire to the dispersive electrode for return to the electrosurgical generator, it is not possible to predict the damaging effects along the random tissue pathway involved. Each of the risks associated with the use of a conventional snare increases as the size of growth to be removed increases.

The conventional electrosurgical snare described above is also known as a monopolar electrosurgical device. The monopolar description applies since only one portion of the electrical circuit, namely the snare wire to tissue interface, is controlled by the user. The second portion of the electrical circuit, namely the dispersive electrode, is at a site removed from the desired site of electrosurgical effect.

To reduce the risks associated with the conventional monopolar electrosurgical snare, attempts have been made to design bipolar electrosurgical snares. In a bipolar electrosurgical device, two electrically separated contacts are incorporated in a single device controlled and maneuvered by the user. One contact acts as the active electrode, the second contact acts as the return electrode. This isolates the electrosurgical effect to the tissue between the two contacts, leading to the conclusion that bipolar electrosurgical devices are intrinsically safer than monopolar electrosurgical devices. The possibility of an unintentional electrosurgical effect at a site removed from the point of contact of the bipolar device is eliminated.

Attempts have been made to incorporate this bipolar concept into the design of electrosurgical snares for the removal of tissue from the body. One such device, U.S. Pat. No. 4,311,143, incorporates a small conductive surface on the exterior of the outer tubular sheath of the snare mechanism to act as the pathway for return of the electrosurgical current to the generator. In this device the wire loop forms the other portion of the electrosurgical circuit. A significant disadvantage of this design, as with conventional monopolar snares, is that the current density along the active wire loop remaining in contact with the tissue growth increases as the loop is withdrawn into the sheath and the diameter of the loop remaining in contact with tissue decreases. This can lead to the same problem associated with monopolar snares, namely, an increasing rate of cutting and a decreasing degree of coagulation with the potential of hemorrhage. Another disadvantage of this design is that the conductive surface acting as a return electrode on the outer surface of the sheath can cause an electrosurgical effect to the normal tissue in an area adjacent to the abnormal tissue being removed rather than isolating the effect to the surface from which the abnormal tissue is being removed. Recognizing that electrical currents will always seek the pathway of least resistance, another disadvantage of this design arises. If the active wire loop is surrounding a large piece of tissue the apparent pathway for electrosurgical current will be through the tissue in contact with the portion of the wire loop closest to the tip of the sheath to the electrode surface on the sheath of this snare. This prevents the desired effect from occurring to the tissue in contact with the portion of the wire loop that is furthest from the tip of the snare sheath. Attempts to increase the electrosurgical effect along the entire portion of the exposed loop of this design by increasing the power level of the generator will only further compound the problem of the pathway of least resistance being sought by this energy. As with conventional monopolar snares, the disadvantage of this design is most obvious when attempts are made to remove larger growths.

Another attempt to incorporate the concept of bipolar electrosurgery into a snare is shown in U.S. Pat. No. 4,493,320. In this design, a loop is formed by two separate conductive wires joined together by an electrically non-conductive material to form a loop. These two electrically conductive wires are electrically separated as they enter the end of the sheath since the sheath has a double lumen. In this device, the entire length of the two wires forming the sides of the loop are electrically conductive. A significant disadvantage of this design, as with conventional monopolar snares, is that the current density along the wire remaining in contact with the tissue growth increases as the wires forming the loop are withdrawn into the sheath and the diameter of the loop remaining in contact with tissue decreases. This can lead to the same problem associated with monopolar snares, namely, an increasing rate of cutting and a decreasing degree of coagulation with the potential of hemmorhage. Once again, recognizing that the pathway of least resistance will always be sought by the electrical currents involved, it is easy to recognize that the greatest electrosurgical effect to tissue captured within this type of loop will occur in the area immediately adjacent to the face of the double lumen sheath, and in the area immediately adjacent to the face of the insulating material that joins the distal ends of the wires to form the loop, since the conductive wires are physically closest together at these points. As soon as adequate drying of the tissue in these areas occurs, the high voltages presented by the typical electrosurgery generator will cause arcing in these areas. This arcing can prevent adequate electrosurgical coagulation from occuring to the remaining tissue surrounded by the extended loop.

In summary, conventional electrosurgical snares do not provide for safe, consistent and predictable electrosurgical results when a given nominal level of electrosurgical current, supplied by the complementary electrosurgical generator, is applied to abnormal tissue growths of varying sizes. By the very nature of the construction of conventional snares, the size of the electrically active loop changes by several magnitudes as the procedure of tissue resection proceeds, leading to the possibility of a dangerously high current density along the remaining exposed loop surface.

OBJECTS OF THE INVENTION

It is an object of the present invention to provide an electrosurgical apparatus for resecting abnormal protruding growths which is capable of providing consistent and predictable electrosurgical results.

Another object of the present invention is to provide an electrosurgical apparatus which is capable of operating in a safe manner.

Another object of the present invention is to provide an electrosurgical apparatus which is capable of significantly reducing the degree to which the current density changes at the loop to tissue interface during the resection of tissue.

Another object of the present invention is to provide an electrosurgical apparatus which is capable of resecting relatively larger tissue growths while reducing the degree to which the current density changes during the resection procedure.

Another object of the present invention is to provide an electrosurgical apparatus which is capable of bipolar operation.

Still another object of the present invention is to provide an electrosurgical apparatus which is capable of eliminating the risk of undesirable and unpredictable electrosurgical effects at sites other than the loop to tissue interface.

SUMMARY OF THE INVENTION

In accordance with the present invention, there is provided an electrosurgical apparatus for resecting abnormal protruding growths which in first embodiment of the invention includes an elongated tubular insulating sheath and a flexible electrically conductive wire which is slideably disposed with respect to the sheath. The wire has a length greater than the length of the sheath and projects from both the proximal and the distal ends of the sheath with the wire forming a loop at the distal end of the sheath. Except for a selected portion of the loop, the wire is covered by an insulating layer.

A handle is attached to the proximal end of the wire for the purpose of sliding the wire relative to the sheath to expand or contract the loop. An actuator assembly is attached to the proximal end of the sheath to facilitate endoscopic insertion of the sheath into the body of a patient. Electrical connections are provided for connection to a monopolar electrosurgical current source.

A dispersive electrode is used for establishing contact between the body of the patient and the electrosurgical current source, thereby completing the electrical circuit.

The selected portion of the loop which is uninsulated presents a fixed length of electrically active wire and therefore a fixed current density, thereby eliminating variation in current density as the loop is varied in size during the resection procedure.

In a second embodiment of the invention, the apparatus operates in a bipolar mode with the distal ends of the wires joined together by a mechanical connector which is electrically insulating and the proximal ends of the wires are connected to a bipolar electrosurgical current source.

The mechanical connection further includes a short segment of electrical insulation disposed on a selected one of said wires forming said loop and disposed adjacent said mechanical connector. This insulating segment brings the uninsulated portions of the wires forming the loop out of alignment with each other and prevents unwanted arcing when the wires are brought close together.

BRIEF DESCRIPTION OF THE DRAWINGS

Other objects and advantages of the present invention will become apparent from the following description taken in connection with the drawings in which.

DETAILED DESCRIPTION OF THE INVENTION

Figure 1:
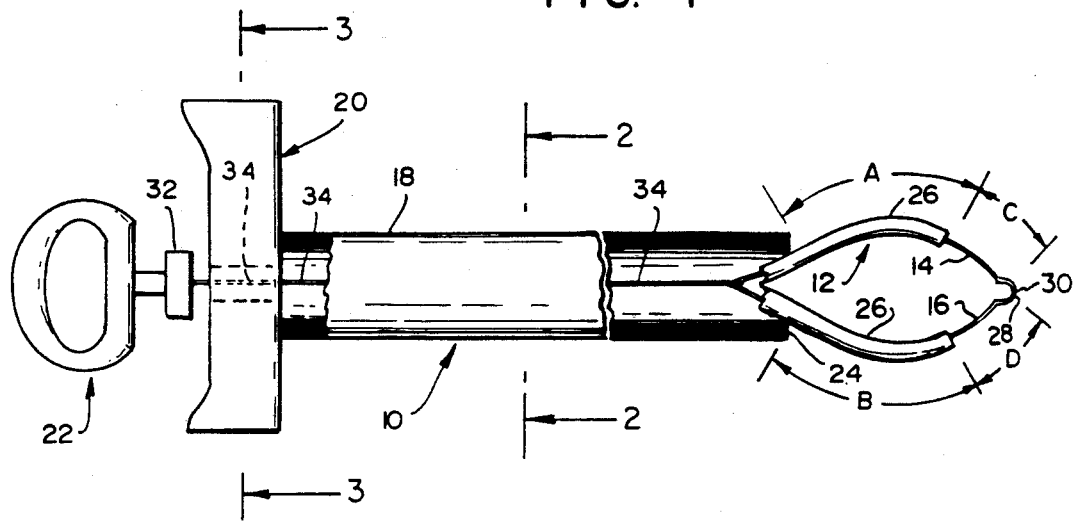
FIG. 1 is a top plan view of an electrosurgical apparatus for resecting abnormal protruding growths made in accordance with the present invention with portions shown partially in section to reveal details of internal construction.
Figure 2:
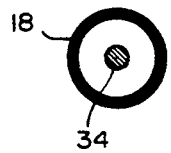
FIG. 2 is a cross-sectional view taken along the line 2—2 of FIG. 1.
Figure 3:
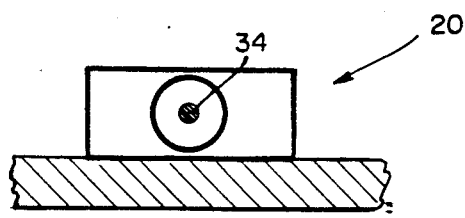
FIG. 3 is a cross-sectional view taken along the line 3—3 of FIG. 1.

With reference to the drawings there is shown in FIG. 1 a primary embodiment of an electrosurgical apparatus for resecting abnormal protruding growths which is generally designated by the reference numeral 10 and which includes: a loop 12 made of electrically conductive wire 14, 16 slideably mounted within a tubular insulated sheath 18 which is connected to an actuator assembly 20 for endoscopic insertion into a patient's body cavities. The wire 14, 16 is connected to a handle assembly 22 that will allow the loop 12 to be extended from or retracted into the distal end 24 of the tubular sheath 18. In accordance with a novel feature of the invention, the loop 12 is covered over a major portion of its circumference by an insulating material 26, leaving only a minor portion of its circumference uninsulated at the portion of the loop 12 most distal from the tubular sheath 18, and electrically active.

The major portion of the circumference of the loop 12 which is insulated, is designated by the reference letters A and B and is preferably in the order of approximately 75% of the total circumference of the loop while the minor portion of the circumference of the loop 12 which is bare, is designated by the reference letters C and D, and is preferably in the order of approximately 25% of the circumference of the loop 12.

Alternatively, the insulated portions of the loop 12, designated by letters A and B, may be in the range of 60 to 90% of the total circumference of the loop, leaving the bare portions of the loop 12, designated by the letters C and D, in the range of 40 to 10% of the circumference of the loop, respectively.

The distal portion 28 of the loop 12 may have a portion of reduced diameter as is indicated by the reference numeral 30 or alternatively, may be formed as a smooth curve continuous with the balance of the loop 12.

The handle assembly 22 incorporates an electrical connector 32 for the purpose of connecting the wire 34 to an electrosurgical generator. The wire 34 is connected to the wires 14, 16 within the sheath 18. FIG. 1 shows the sheath 18 partially broken away to show the connection of the wires 14, 16 and 34.

The handle assembly 22, the actuator assembly 20, the electrical connector 32, and the electrosurgical generator are all conventional in nature and, therefore, have not been described in detail.

In this monopolar electrosurgical embodiment of the invention 10, the exposed electrically conductive portion of the loop portions C and D comprises one pole of the electrosurgical circuit while a large surface area dispersive electrode, in contact elsewhere with the body of the patient, forms the second pole, completing the circuit to the electrosurgical generator. The dispersive electrode is conventional in nature and has, therefore, not been illustrated.

The advantage of the present invention 10 compared to conventional electrosurgical snares, is provided by the fact that a known length of electrically conductive wire is in contact with the tissue to be treated, whether the snare is 100% extended, 50% extended, 25% extended, or only 10% extended. The present invention 10 allows nominal electrosurgical power levels that are significantly lower than the levels used with conventional electrosurgical snares to be used to resect large tissue growths while, at the same time maintaining a clinically effective current density along the electrically active portion (C and D) of the snare loop 12. Because the same nominal electrosurgical power level will be used to treat growths of varying sizes, the user will be able to obtain more predictable and safer results. This nominally lower electrosurgical power level will minimize the risk of undesirable deep thermal injury and tissue damage or burns at alternate sites.

To fully eliminate any risk of tissue damage or burns at alternate body sites, a second embodiment of the invention 100 is configured as a bipolar electrosurgical device, which includes a pair of elongated flexible electrically conductive wires 102, 104 which are covered by an insulating layer 106, 108. This pair of insulated wires 102, 104 is mounted within a tubular cover sheath 110 having a proximal end 112 and a distal end 114, and made of an electrically insulating material. The two wires 102, 104 extend from the proximal 112 and the distal ends of the tubular cover sheath 110. At the proximal end 112 of the tubular cover sheath 110 the two wires 102, 104 are attached to a handle assembly which is not illustrated but which is generally similar to the actuator assembly 20 of FIG. 1 and which allows the two wires 102, 104 to remain electrically separated. This handle assembly allows the two wires 102, 104 to be advanced or retracted within the tubular outer sheath 150 which slideably covers the tubular cover sheath 110. The tubular cover sheath 110 provides additional stability to the apparatus 100. The handle assembly also incorporates a means of connecting the two wires 102, 104 to a bipolar electrosurgical generator which is conventional in nature and is not illustrated.

When the handle assembly is advanced, the two wires 102, 104 are extended from the distal end 149 of the tubular outer sheath 150. The distal tips 116, 118 of the two snare wires 102, 104 are joined together by an electrically insulated connector 120. The portions 122, 124 of the two snare wires 102, 104 extending beyond the distal end 114 of the tubular cover sheath 110 form a loop 126, the maximum size of this loop 126 being accomplished when the handle assembly is in its most forward or advanced position.

When the handle assembly is fully retracted, the two snare wires 102, 104, as well as the insulating connector 120 at the distal tips 116, 118 of the snare wires 102, 104, are fully retracted within the distal end 149 of the tubular outer sheath 150. This advancing and retracting motion of the handle assembly allows the size of the extended loop 126 to be varied.

Figure 4:
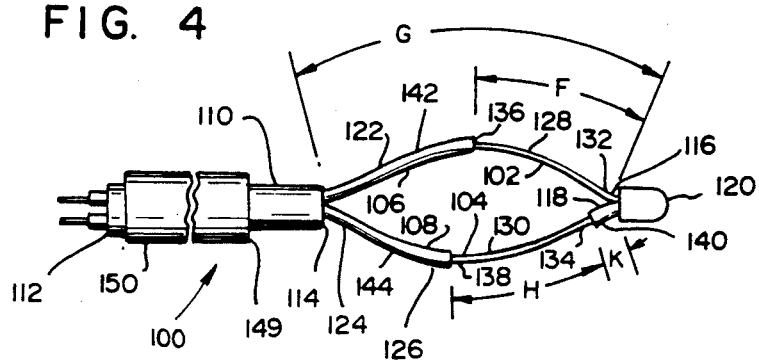
FIG. 4 is a top plan view of a second embodiment of the electrosurgical apparatus of FIG. 1 which is configured by bipolar operation.

To form the electrically active portion 128 of the snare loop 126, the insulating layer 122 is removed from the most distal portion of one of the snare wires 102 along a length designated by the letter F in FIG. 4 which has a preferred range equal to approximately 10% to 40% of the total length of the snare wire that extends beyond the distal end 114 of the tubular cover sheath 110, designated by the letter G, as provided by the range of motion of the handle assembly. The preferred value of the length F is in the order of 25% of the length G. An equal portion of insulation designated by the letter H is removed from the second snare wire 104 beginning at a position adjacent the portion designated by the letter K in FIG. 4 which is preferably in the order of approximately 0.100 inches from the distal tip 118 of the second snare wire 104. When the insulation is removed as described, the loop 126 of the snare will have two electrically conductive portions 128, 130 of approximately equal length. The distal 132, 134 and the proximal ends 136, 138 of these electrically active sections are offset, in parallel relationship to each other, by an amount equal to the short section of insulation 140 remaining on the most distal portion of the second snare wire 104.

The portion designated by the letter K may be in the range of 0.010 to 0.20 inches in length and remains insulated. As indicated above, the portion designated by the letter K has a preferred length in the order of 0.10 inches.

In an alternative embodiment of the invention, which is not illustrated, the portion of the wire designated by the letter F may have a length which ranges from about 20% to about 250% of the portion of the wire designated by the letter H.

Figure 5A:
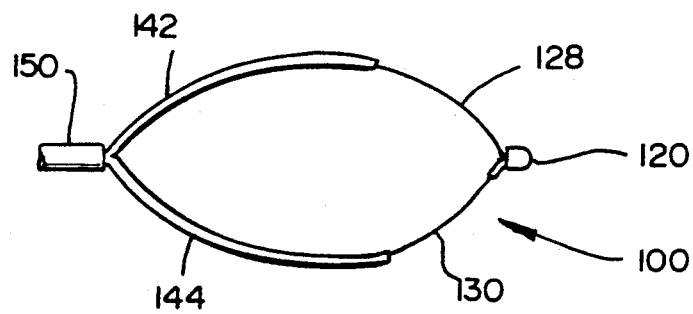
FIG. 5A is a top plan view similar to FIG. 4 drawn to a smaller scale showing the electrosurgical apparatus at the start of a resection procedure.
Figure 5B:
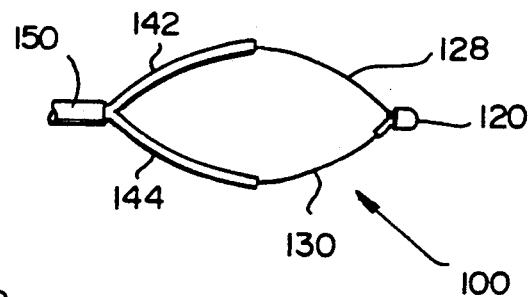
FIG. 5B is a top plan view similar to FIG. 5A showing the electrosurgical apparatus during an intermediate point in the resection procedure.
Figure 5C:
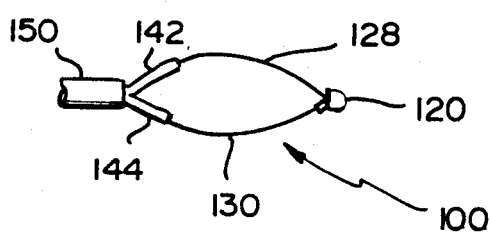
FIG. 5C is a top plan view similar to FIG. 5B showing the electrosurgical apparatus during a further point in the resection procedure.

As previously described, the present invention 100 allows the size of the electrosurgical loop to be varied by means of the handle assembly. One advantage of the apparatus 100 according to the present invention, is provided by having only a known portion of the maximum loop size electrically active; because a known length of electrical conductor will be in contact with the tissue captured within the loop 126 whether the loop is 100% extended, 50% extended, 25% extended or 10% extended; the same nominal power level provided by the bipolar generator will provide equally effective, predictable and safe clinical results in each case. The preferred range of operation is 10% to 40% extended. The portion 142, 144 of the loop 126 that is insulated helps capture tissue growths of varying sizes, but does not adversely affect the electrical performance of the snare by changing the current density along the portion of the loop 126 that remains in contact with the tissue as the loop 126 is retracted within the tubular outer sheath 150 as is shown in FIGS. 5A, 5B and 5C.

Another advantage of the present invention 100 is provided by the insulation 142, 144 that covers approximately 75% of the fully extended portion of the two wires 102, 104 forming the electrosurgical loop 126. As the wires 102, 104 forming the loop 126 are retracted within the tubular sheath 110, the insulation 140, 142, 144 described prevents arcing that would occur between the two wires 102, 104 if they had electrically conductive exposed surfaces that could come into direct contact with each other as soon as the size of the extended loop is reduced below its maximum extended size. As treatment is delivered to the tissue captured within the loop 126 and the loop is retracted within the tubular outer sheath 150, the tissue in direct contact with the 10% to 40% of the snare wire 102, 104 that is electrically active will be satisfactorily coagulated by the time the snare is 60% to 90% or more retracted within the sheath 150. At this point, further electrical treatment of the captured tissue is not required, and the remaining tissue is mechanically sheared as the loop is fully retracted within the tubular sheath.

Another advantage of the present invention 110 is offered by the short segment of insulation 140 that remains at the most distal tip 116 of one of the snare wires 104. This segment of insulation 140 prevents arcing of the typical high voltages necessary to provide effective clinical results between the two electrically conductive segments 128, 130 at the point where they are in very close proximity as they enter the insulated connector 120 tip. By preventing arcing at this point, electrosurgical energy is forced to travel through the tissue that is captured between the two electrically active segments of the snare loop 126.

Still another advantage of the present invention 100 is provided by the fact that the electrical separation of the two exposed portions 128, 130 of the snare loop 126 form a bipolar electrosurgical circuit. As a result, the electrosurgical effect on tissue is isolated to the tissue captured within or between the two wire segments forming this bipolar electrosurgical circuit. This entirely eliminates the possibility of electrosurgical burns or adverse affects to tissue at sites removed from the actual point of treatment. Further, it minimizes the chances of deep thermal injury in the area of treatment since electrosurgical affect is limited to only the plane across the tissue growth captured within the snare.

Figure 6:
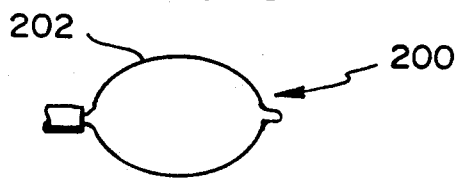
FIG. 6 is a top plan view of the second embodiment of the electrosurgical apparatus shown in FIG. 4 showing an oval pre-bent wire embodiment.
Figure 7:
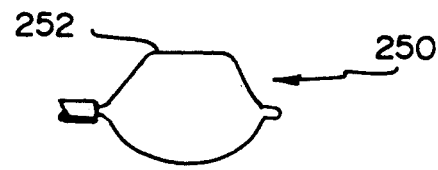
FIG. 7 is a top plan view similar to FIG. 4 showing a crescent pre-bent wire embodiment.
Figure 8:
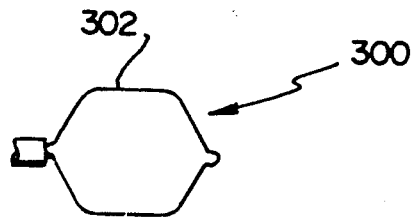
FIG. 8 is a top plan view similar to FIG. 4 showing a hexagonal pre-bent wire embodiment.

In additional embodiments 200, 250, 300 shown in FIGS. 6, 7 and 8, the wires 102, 104 forming the extended loop 126 may be pre-bent to assume a desired shape. Examples of such shapes include: oval 202, crescent 252, and hexagonal 302 shapes.

The wire used for the various embodiments of the invention is preferably a multi-strand stainless steel wire having a diameter in the range of 0.010 to 0.020 inches with a preferred diameter in the order of 0.015 inches.

While preferred embodiments have been shown and described herein, it is obvious that numerous additions, changes and omissions may be made in such embodiments without departing from the spirit and scope of the invention.

What is claimed is:

1. An electrosurgical apparatus for resecting abnormal protruding growths comprising
    an elongated tubular electrically insulating sheath member having a proximal and a distal end,
    a pair of elongated flexible electrically conductive wires with said wires disposed within said sheath and having a length greater than said sheath such that said wires each extend from both said proximal and said distal ends of said sheath with said wires each having proximal and distal ends,
    electrically insulating connector means disposed at said distal ends of said wires for the purpose of mechanically connecting said distal ends of said wires to form a loop projecting from said distal end of said sheath and with said wires electrically insulated from each other and with said loop having a proximal and a distal portion, electrical insulation means disposed covering all but a selected portion of each of said elongated wires which forms said loop, where said electrical insulation means covers the distal end of one of said wires, handle means for sliding said wires relative to said sheath to expand or contract said loop, electrical connection means for connecting said proximal ends of said wires to a bipolar electrosurgical current source means.

2. An electrosurgical apparatus according to claim 1 in which said electrical insulation means comprises
a distal electrical insulator segment covering a portion of one of said wires adjacent to said electrically insulating connector means and another electrical insulator segment spaced from said distal electrical insulator segment on said wire.

3. An electrosurgical apparatus according to claim 2 in which said distal electrical insulator segment is in the order of one hundred thousandths of an inch long.

4. An electrosurgical apparatus according to claim 2 in which said distal electrical insulator segment is in the range of ten thousandths to two hundred thousandths of an inch long.

5. An electrosurgical apparatus according to claim 2 further comprising a pair of bare wire portions formed by said electrical insulation means and formed, one each, on said pair of elongated wires and disposed at said distal ends of said wires and with said bare wire portions offset relative to each other.

6. An electrosurgical apparatus according to claim 5 in which said bare wire portions are offset relative to each other by an amount substantially equal to said distal electrical insulator segment which is disposed on one of said wires adjacent to said electrically insulating connector means.

7. An electrosurgical apparatus according to claim 2 in which said distal electrical insulator segment has a preferred range of fifty thousandths to two-hundred thousandths of an inch long.

8. An electrosurgical apparatus according to claim 1 in which said electrical insulation means is non-symmetrically located on said loop formed by said wires.

9. An electrosurgical apparatus according to claim 1 in which said selected portion of said loop comprises the distal portion of said loop.

10. An electrosurgical apparatus according to claim 1 in which said selected portion of said loop comprises a portion which is the order of 25% of the circumference of said loop.

11. An electrosurgical apparatus according to claim 1 in which said selected portion of said loop comprises a portion which is in the range of 10 to 40% of the circumference of said loop.

12. An electrosurgical apparatus according to claim 1 in which each of said wires has a diameter in the order of fifteenthousandths of an inch.

13. An electrosurgical apparatus according to claim 1 in which each of said wires is a multi-strand wire.

14. An electrosurgical apparatus according to claim 1 in which each of said wires has a preferred diameter in the range of ten to twenty thousandths of an inch.

15. An electrosurgical apparatus according to claim 1 in which each of said wires is made of stainless steel.

16. An electrosurgical apparatus according to claim 1 in which said loop is pre-bent to form an oval configuration.

17. An electrosurgical apparatus according to claim 1 in which said loop is pre-bent to form a hexagonally shaped configuration.

18. An electrosurgical apparatus according to claim 1 in which said loop is pre-bent to form a crescent shaped configuration.

19. An electrosurgical apparatus according to claim 1 further comprising
actuator means mounted on said proximal end of said sheath for endoscopic insertion of said distal end of said sheath into a patient's body.

20. An electrosurgical apparatus according to claim 1 in which said wires are further defined as a first wire and a second wire with said insulation removed from a selected portion of said first wire which forms said loop and from a selected portion of said second wire which forms said loop and with said selected portion of said second wire of a length having a range from about 20% to about 250% of the length of said selected portion of said first wire.

21. An electrosurgical apparatus according to claim 1 in which said wires are further defined as a first wire and a second wire with said insulation removed from a selected portion of said first wire which forms said loop and from a selected portion of said second wire which forms said loop and with said selected portion of said second wire of a length having a range from less than the length of the selected portion of the first wire to a length greater than the length of the related portion of the first wire.

* * * * *